United States Patent [19]
Cohen et al.

[11] Patent Number: 5,643,257
[45] Date of Patent: Jul. 1, 1997

[54] APPARATUS AND METHOD FOR VENOUS LIGATION

[75] Inventors: Donald Cohen, Irvine; Derek J. Daw, Costa Mesa, both of Calif.; George F. Kick, Medina, Ohio; George M. Acosta, Long Beach, Calif.

[73] Assignee: Endovascular, Inc., Costa Mesa, Calif.

[21] Appl. No.: 412,170

[22] Filed: Mar. 28, 1995

Related U.S. Application Data

[62] Division of Ser. No. 183,994, Jan. 18, 1994, Pat. No. 5,437,664.

[51] Int. Cl.⁶ .................................................. A61B 17/36
[52] U.S. Cl. ................................ 606/48; 606/41; 606/42; 606/40; 128/898
[58] Field of Search .................................. 606/1, 32–34, 606/37–42, 45–52; 128/898, 642; 607/100–102, 115, 116

[56] References Cited

U.S. PATENT DOCUMENTS

| | | | |
|---|---|---|---|
| 3,858,586 | 1/1975 | Lessen | 606/49 |
| 4,057,063 | 11/1977 | Gieles et al. | 606/38 |
| 5,190,517 | 3/1993 | Zieve et al. | 606/38 |
| 5,437,664 | 8/1995 | Cohen et al. | 606/42 |

OTHER PUBLICATIONS

Brunelle et al., "A Bipolar Electrode for Vascular Electrocoagulation with Alternating Current", Radiology, vol. 137, pp. 239–240, Oct. 1980.

Ogawa et al., "Electrothrombosis as a Treatment of Cirsoid Angioma in the Face and Scalp and Varicosis of the Leg", Plastic and Reconstructive Surgery, vol. 70, No. 3, Sep. 1982.

"The Medical Letter—Electrofulguration for Varicose Veins", The Medical Letter on Drugs and Therapeutics, vol., 14, Issue 248, pp. 53–55, Jul. 1968.

*Primary Examiner*—Angela D. Sykes
*Assistant Examiner*—Michael Peffley
*Attorney, Agent, or Firm*—John L. Rogitz

[57] ABSTRACT

A minimally-invasive surgery apparatus for causing the lumen of a vein to collapse to prevent blood flow through the vein, e.g., a varicose vein or a side branch of the saphenous vein, includes an electrode which is electrically connected to a power source, and the electrode is percutaneously advanced into the vein. Then, the power source is activated to energize the electrode and thus the blood vein until the blood vein sufficiently collapses to block the lumen of the vein. A feedback loop is also provided for sensing electrical impedance of the tissue within the vein being energized and for deenergizing the electrode when the impedance reaches a predetermined value.

5 Claims, 3 Drawing Sheets

APPARATUS AND METHOD FOR VENOUS LIGATION

This application is a divisional of application Ser. No. 08/183,994, filed Jan. 18, 1994, now U.S. Pat. No. 5,437,664.

FIELD OF THE INVENTION

The present invention relates generally to endoscopic surgical tools. More particularly, the present invention relates to endoscopic apparatus and methods for closing blood vessels. The present invention particularly, though not exclusively, relates to endoscopic treatment of varicose veins.

BACKGROUND

Certain surgical treatments require the modification or removal of blood veins from the body. For example, the treatment of varicose veins sometimes requires the varicose veins to be removed from the body in an invasive, painful, slow-healing, and time-consuming procedure. Also, the saphenous vein is surgically modified during a procedure, known as in situ saphenous vein bypass, for alleviating conditions caused by reduced blood flow through an occluded femoral artery.

In situ saphenous vein bypass is a procedure in which the saphenous vein in a human leg, which normally returns venous blood from the ankle upwardly through the leg, is anastomosed to the femoral artery at an upstream (proximal) location on the artery and a downstream (distal) location on the artery to assume the function of the femoral artery, i.e., to deliver arterial blood to the leg. Such a bypass procedure may be required when the femoral artery has become too occluded or otherwise impaired between the upstream and downstream locations to transport the flow of blood required of it.

When the saphenous vein is to assume the function of the femoral artery, it becomes necessary to close off, i.e., to ligate, so-called "side branch" blood veins. These side branch veins are generally smaller than the saphenous vein and are colloquially known as "tributaries" when they lead to the saphenous vein and "perforators" when they lead to deeper venous circulation. Side branches ordinarily establish pathways for venous blood into the saphenous vein for returning the blood to the heart and lungs. Accordingly, to prevent the unwanted flow of arterial blood directly into the venous system via the saphenous vein, the side branches and perforators must be ligated. Stated differently, by ligating the side branches, arterial blood which is permitted to flow through the saphenous vein and thereby bypass the occluded segment of the artery is prevented from invading the venous system through the side branches.

Typically, side branches are ligated by constricting the side branches with sutures. Unfortunately, ligating side branches with sutures can be time-consuming and labor-intensive, because all the side branches must be located either by making a large number of small incisions in the leg or by making one very large incision. Also, it is difficult to ligate side branches with sutures in less-invasive procedures, i.e., endoscopically.

As recognized by the present invention, side branches of the saphenous vein may be ligated in less invasive procedures. More particularly, the present invention recognizes that blood flow through side branches of the saphenous vein can be quickly and easily stopped by advancing an electrode into the side branch and energizing the electrode to cause the tissue to coagulate and thereby block fluid flow through the side branch. As further recognized by the present invention, varicose veins can be quickly and easily treated by ligating them in less invasive procedures. Thereby, unsightly discolorations in the leg attributable to varicose veins can be eliminated in an out-patient procedure.

Although coagulating devices have been introduced for other surgical applications, these devices typically have bulky components which are designed for use within a relatively large body cavity that has been exposed by surgery. Consequently, existing coagulating devices cannot easily be used to stop blood flow from "hard-to-reach" sources, such as saphenous vein side branches. Furthermore, existing coagulating devices cannot easily be used in less-invasive surgery for the treatment of varicose veins.

Moreover, many coagulating devices function simply by applying electricity to tissue. The length of time the tissue is exposed to the electricity is controlled by the surgeon, usually by depressing a foot pedal linked to a source of electricity, e.g., a Bovie model generator made by Valley Labs of Colorado. Consequently, tissue can easily be unintentionally overheated, thereby causing unwanted scabbing, charring, and other unnecessary tissue damage. Such damage can be particularly onerous in certain circumstances, e.g., saphenous vein side branch ligation and varicose vein treatment. Indeed, excessive electro-ligation of varicose veins in an attempt to reduce discoloration caused by the veins may be a cure that is worse than the disease. Stated differently, applying rf energy to a blood vein over excessive time periods or at excessively high power can result in arcing and perforation of vein.

It is therefore an object of the present invention to provide a device that can less-invasively ligate side branches of a saphenous vein. Another object of the present invention is to provide an apparatus and method for less invasive treatment of varicose veins. Still another object of the present invention is to provide an apparatus and method for less invasive surgical ligation which is easy to use and cost-effective to manufacture.

SUMMARY OF THE INVENTION

A device for use in endoscopic surgery to inhibit blood flow through a blood vessel includes an elongated electrical conductor which has a distal end. Preferably, the conductor includes a segment that is bendable into a predetermined shape, and a direction indicator may be provided for indicating the direction in which the conductor is bent.

A source of electricity is electrically connected to electrical conductor. As intended by the presently preferred embodiment, the source of electricity generates an rf output sufficient to cause the blood vessel to collapse and insufficient to perforate the blood vessel. Also, an electrically insulative smooth flexible sheath surrounds at least a segment of the conductor. In accordance with the present invention, the sheath has an outside diameter of less than one millimeter (1 mm) to permit easily slidably engaging the sheath with the lumen of the blood vessel.

An electrode is connected to the distal end of the electrical conductor such that the source of electricity can be energized to energize the electrode to thereby cause the lumen of the blood vessel to collapse when the electrode is positioned in the vessel. In one presently preferred embodiment, the electrode extends beyond a distal end of the sheath, and the length of the electrode is approximately equal to the diameter of the blood vessel. Advantageously, the electrode is formed integrally with the conductor, and the electrode includes a rounded distal tip. Further, the electrode preferably includes an anti-sticking coating which is deposited on the electrode.

Preferably, a feedback device is provided for sensing a preselected parameter of the blood vessel. The feedback device generates a signal when the preselected parameter reaches a predetermined value, and the preselected parameter is affected by the treatment of the preselected portion of tissue. The preselected parameter can be temperature, in which case the feedback device includes a temperature sensor secured to the apparatus for sensing the temperature of the electrode.

Alternatively, the preselected parameter is at least one electrical parameter selected from the group of parameters consisting of: source of electricity output voltage, time rate of change of source of electricity output voltage, source of electricity output power, time rate of change of source of electricity output power, source of electricity output current, time rate of change of source of electricity output current, tissue electrical impedance, time rate of change of tissue electrical impedance.

In another aspect of the present invention, an apparatus which is connectable to a power source for electrically ligating a preselected portion of tissue includes an electrically insulative sheath configured for slidably engaging a lumen of a body vessel. Additionally, the apparatus includes an electrode which is positioned in the sheath. As intended by the present invention, the electrode is electrically connectable to the power source for energizing the preselected portion of tissue when the electrode is positioned adjacent the preselected portion of tissue and the power source is activated to provide power to the electrode. A feedback device is provided for sensing a preselected parameter and for generating a signal representative of the magnitude of the preselected parameter. In accordance with the present invention, the preselected parameter is affected when the preselected portion of tissue is energized by the electrode.

In still another aspect of the present invention, a method is disclosed for treating a varicose vein. The method includes the steps of providing an electrically energizable electrode, and then percutaneously advancing the electrode into the varicose vein such that the electrode is juxtaposed with the wall of the varicose vein. Next, contact is established between the wall of the varicose vein and the electrode, and the electrode is energized until the vein collapses around the electrode to thereby block blood flow through the vein.

In yet another aspect of the present invention, a method is disclosed for electro-ligation of a blood vessel. The method includes the steps of providing an electrically energizable electrode and an endoscopic instrument, and disposing the electrode in the instrument. Then, the instrument is percutaneously advanced with electrode into the blood vessel, and the electrode is energized until the vessel collapses around the electrode to thereby block blood flow through the vein.

The details of the present invention, both as to its construction and operation, can best be understood in reference to the accompanying drawings, in which like numerals refer to like parts, and which:

DETAILED DESCRIPTION OF THE PREFERRED EMBODIMENT

Figures 1, 2:
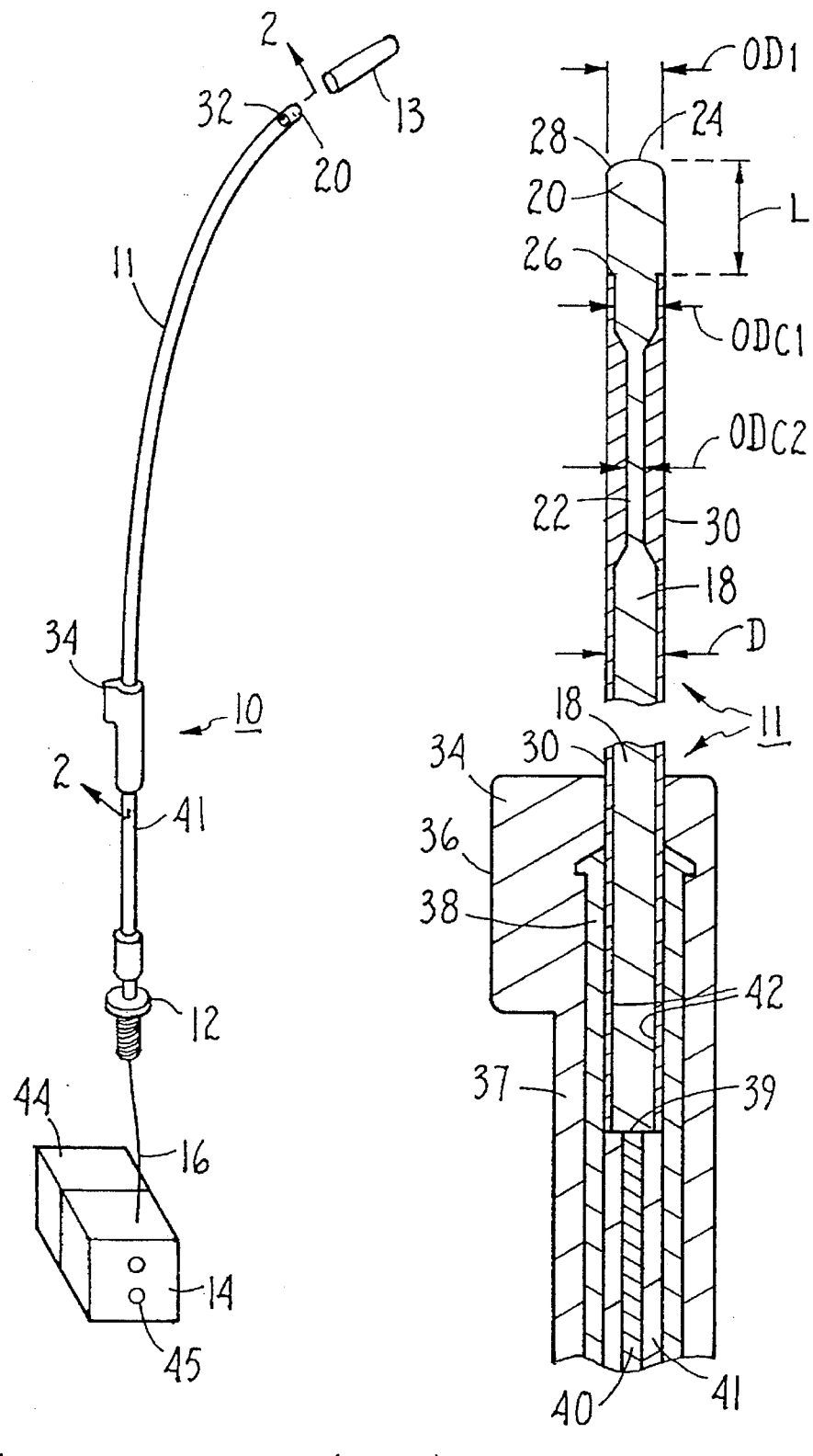
FIG. 1 is a perspective view of the apparatus for venous ligation of the present invention.
FIG. 2 is a cross-sectional view of the apparatus for venous ligation of the present invention, as seen along the line 2—2 in FIG. 1.

Referring initially to FIG. 1, an endoscopic electrocauterizer for closing off side branches of blood veins and for blocking blood flow through varicose veins is shown, generally designated 10. While the discussion below focusses on side branch closure and varicose vein treatment, it is to be understood that the principles of the present invention disclosed below can be applied to a wide variety of medical treatments requiring tissue cauterization, including perforator vein treatment, hemorrhoid treatment, and neurosurgery applications.

As shown in FIG. 1, the cauterizer 10 includes a probe 11 and a connector body 12. The connector 12 is preferably a standard banana plug connector, and can be connected to a source 14 of electrical power via an electrical line 16. The source 14 can advantageously be a Bovie generator made by Valley Laboratories of Colorado.

It is to be understood that the probe 11 can be percutaneously advanced into a blood vessel, e.g., a varicose vein, or that it could be engaged with the lumen of an endoscopic surgery instrument 13, and then the instrument 13 with probe 11 advanced into, e.g., the side branch of a saphenous vein. As intended by the present invention, the instrument 13 can be any one of the instruments disclosed in the following U.S. patent applications, all of which are assigned to the sole owner of the assignee of the present invention: Ser. No. 07/867,841, filed Apr. 13, 1992 for an invention entitled "FLEXIBLE TIP CATHETER"; Ser. No. 07/954,120, filed Sep. 29, 1992 for an invention entitled "FLEXIBLE ENDOSCOPE WITH HYPOTUBE ACTIVATING WIRE"; and Ser. No. 07/970,402, filed Nov. 2, 1992 for an invention entitled "ENDOSCOPE FOR SHUNT PLACEMENT", all of which are incorporated herein by reference.

In cross-reference to FIGS. 1 and 2, the probe 11 includes an elongated electrical conductor 18 having a cylindrically-shaped electrode 20 formed integrally on the distal end of the conductor 18. Preferably, the conductor 18 has an electrical resistance below ten ohms per foot ($10\Omega/ft$). In the preferred embodiment, the conductor 18 with electrode 20 is made of type 304 stainless steel. By manufacturing the electrode 20 integrally with the conductor 18, manufacturing costs of the probe 11 are minimized, and a firm connection is established between the electrode 20 and the conductor 18.

FIG. 2 shows that the conductor 18 has an outside diameter $OD_{C1}$ of about eighteen thousandths of an inch (0.018"). Also, the conductor 18 tapers radially inwardly to a bendable segment 22 having an outside diameter $OD_{C2}$ of about ten thousandths of an inch (0.010"). As the skilled artisan will appreciate, the bendable segment 22 is malleable and flexible. Consequently, the segment 22 can be bent into a predetermined curvilinear shape, as shown in FIG. 1, to facilitate advancing the probe 11 into a side branch and to facilitate contact between the electrode 20 and the wall of a varicose vein into which the probe 11 has been advanced.

As shown best in FIG. 2, the electrode 20 is formed with a rounded distal tip 24. An abutment surface 26 is established by the electrode 20, and the abutment surface 26 radially projects beyond the conductor 18. Preferably, the electrode 20 has an outer diameter $OD_1$ of between about twenty eight thousandths of an inch and eighty four thousandths of an inch (0.028"–0.084"), and more preferably the outer diameter $OD_1$ is about seven-tenths of a millimeter (0.7 mm).

The length L of the electrode 20 is between about one to ten millimeters (1–10 mm). Specifically, the length L is established to be approximately equal to the maximum diameter of the blood vein into which the probe 11 is advanced. More specifically, for blood veins having a diameter of about four to six millimeters (4 mm–6 mm), the length L of the electrode 20 is about four millimeters (4 mm). Also, for blood veins having a diameter of about six to eight millimeters (6 mm–8 mm), the length L is about six millimeters (6 mm). Further, for blood veins having a diameter larger than eight millimeters (8 mm), the length L is about eight millimeters (8 mm).

In the presently preferred embodiment, a non-sticking, non-insulative substance 28 is deposited on the surface of the electrode 20 to inhibit sticking of the electrode 20 to body tissue during energization of the electrode 20. Preferably, the substance 28 is chrome which is deposited on the electrode 20 by vapor deposition. Alternatively, the electrode 20 can be coated with titanium nitrate or Teflon®.

FIG. 2 also shows that an insulative sheath 30 surrounds the conductor 18 and abuts the abutment surface 26 of the electrode 20. As can be seen in FIG. 2, the outer surface of the sheath 30 is flush with the outer surface of the electrode 20. In accordance with the present invention, the sheath 30 is bonded to the conductor 18 with a high-temperature epoxy.

As intended by the present invention, the sheath 30 is made of an electrically resistive, smooth, biocompatible material, such as PEBAX® made by Atochem, Inc. of New Jersey, or TFE Teflon®, which typically has a dielectric strength of about seven hundred to one thousand volts per mil of material (700–1000 v/mil). Also, the sheath 30 is made of a material which will not easily melt or breakdown under the high temperatures that are typically generated during electrocautery. Further, the sheath 30 should be made of a material that has a low coefficient of friction.

PBax® is the presently preferred material of choice for the sheath 30 in light of its above-mentioned attributes and because it is relatively flexible, elastic, and has a low coefficient of friction. These attributes permit the sheath 30 to be easily advanced through a potentially curvilinear, small-diameter lumen of blood vein or an endoscopic instrument. Further to this end, the outside diameter OD of the sheath 30 (and, hence, the outside diameter of the probe 11) is preferably equal to less than about one millimeter (1 mm). In one presently preferred embodiment, the outside diameter OD of the sheath 30 is between about twenty eight thousandths of an inch and ninety two thousandths of an inch (0.028"–0.092"). Alternative materials which can be used for the sheath 30 include polyimide, polyethylene, and polypropylene.

If desired, a sensor 32 (FIG. 1) can be attached to the electrode 20. The sensor 32 can be a thermocouple, thermistor, or other suitable temperature-sensing device. Alternatively, the sensor 32 can be a pressure sensor for sensing fluid pressure at the distal end of the probe 11.

FIG. 2 shows that a flat, generally paralellepiped-shaped bend indicator 34 is bonded to the sheath 30. As shown, the indicator 34 is formed with a projecting edge 36 that is distanced from the sheath 30. As intended by the present invention, the bend indicator 34 is oriented during manufacturing such that the projecting edge 36 extends outwardly in the same direction as the bend of the bendable segment 22 of the conductor 18. The indicator 34 remains outside the patient's body during surgery, and the operator of the cauterizer 10 can consequently ascertain during surgery the direction in which the bendable segment 22 of the conductor 18 has been bent.

FIG. 2 shows that the bend indicator 34 is formed integrally with a metal jacket 37, and the jacket 37 surrounds the sheath 30 to transmit torque to the probe 11. An insert 38 made of silicone rubber is disposed between the jacket 37 and sheath 30. Further, the probe 11 has a proximal end 39, and a high voltage line, including a high voltage lead 40 and high voltage insulator 41, abuts the proximal end 39 of the probe 11. A wire 42 is soldered to the high voltage lead 40 and conductor 18 to further ensure electrical contact between the two components. It is to be appreciated that the high voltage lead 40 in turn is electrically connected to the source 14 of electricity via the line 16 and plug 12 (FIG. 1).

In the operation of the cauterizer 10, reference is made to FIGS. 1 and 2. The plug 12 is electrically connected to the source 14 of electricity. Thus, both the sensor 32 and electrode 20 of the probe 11 are electrically connected to the source 14 of electricity.

The source 14 can be electrically connected to a microprocessor 44 which is advantageously a type "486" microprocessor. As disclosed more fully below, the microprocessor 44 is electrically connected to the source 14, and the microprocessor 44 generates a control signal for controlling the source 14 in response to, inter alia, signals from the sensor 32. If desired, indicators 45 can be provided for displaying cauterizer 10 voltage, current, impedance, temperature, and other parameters, in accordance with the operation of the cauterizer 10 disclosed below.

Next, for side branch electro-ligation, the probe 11 is advanced into the working channel lumen of the instrument 13. Then, the instrument 13 into which the probe 11 has been advanced is itself advanced into the blood vein of a patient. The electrode 20 of the probe 11 can be selectively advanced out of the lumen in which it is slidably disposed, and the source 14 of electricity activated to electro-ligate a localized portion of tissue. The probe 11 is then retracted from the vein of the patient. As intended by the present invention, the power level of the source 14 is sufficient to cause the vein to collapse, but insufficient to perforate the vein. To this end, when the source 14 is a Bovie model generator, the so-called "cut" waveform (i.e., a 500KHz sinusoidal rf signal) setting is used.

Alternatively, for varicose vein treatment, the probe 11 itself is percutaneously advanced into the vein, and the wall of the vein is manually urged against the electrode 20. Then, the electrode 20 is energized to cause the wall of the vein to substantially collapse inwardly, thereby blocking blood flow through the vein. The electrode 20 is then retrieved from the vein.

It is to be understood that while the cauterizer 10 disclosed above is a monopolar device, it may also be a bi-polar device, e.g., the cauterizer 10 can have electrodes configured like those disclosed in co-pending U.S. patent application Ser. No. 08/054,123, filed Apr. 26, 1993, for an invention entitled "BiPolar Electrocauterizer", assigned to the sole owner of the present invention and incorporated herein by reference.

Figure 3:
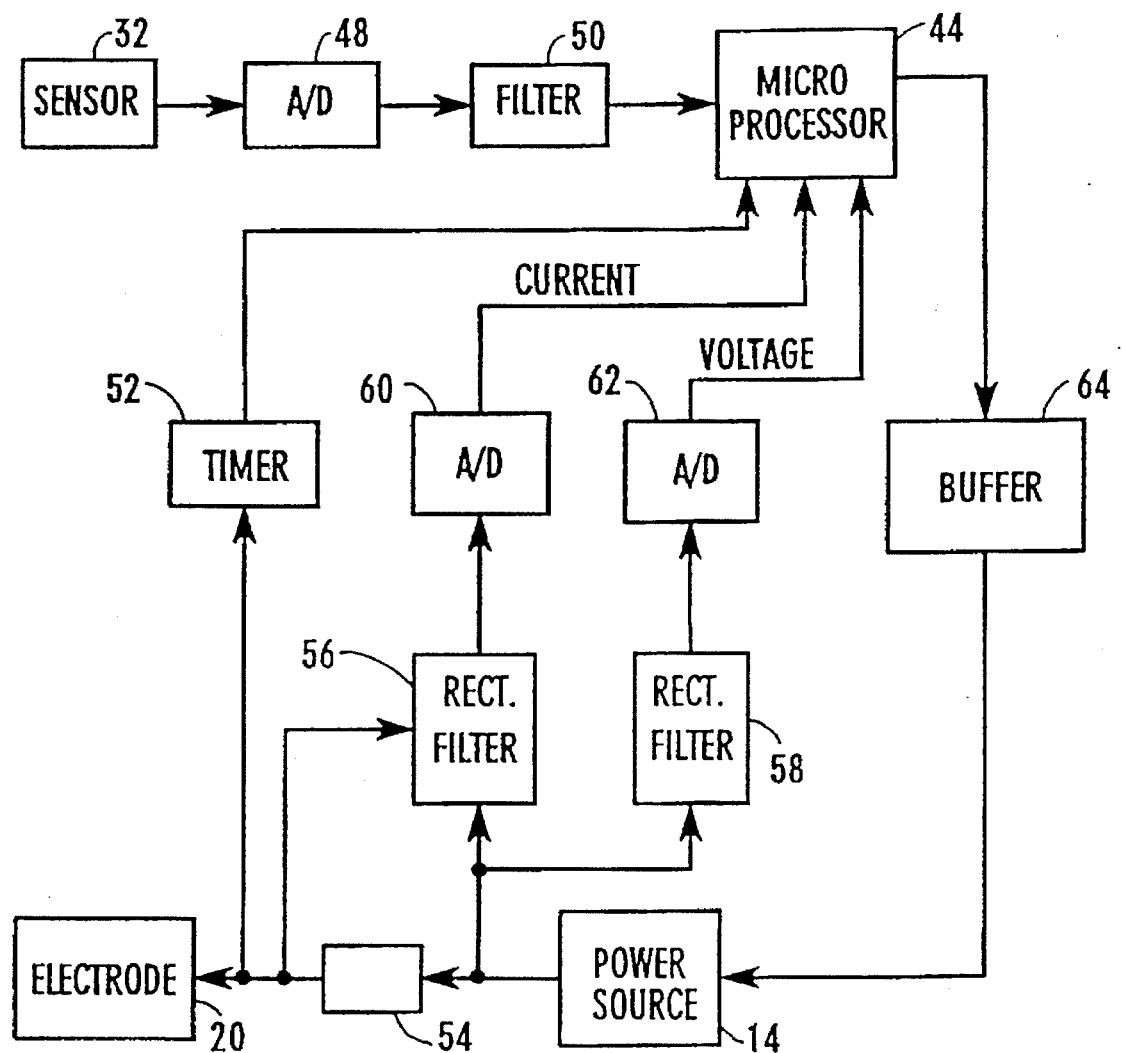
FIG. 3 is a block diagram of the electrical components of the apparatus shown in FIG. 1.

Now referring to FIG. 3, the electrical components of the cauterizer 10 can be seen. As shown, the sensor 32 is connected to an analog-to-digital ("A/D") converter 48, for converting the analog temperature signal from the sensor 32 into a digitized signal. The A/D converter 48 can advantageously be a type AD57804P converter made by Burr Brown, or some other suitable converter known in the art.

FIG. 3 further shows that the A/D converter 48 is connected to a noise filter 50. The noise filter 50 can be a hardware or, more preferably, software filter which filters noise from the digitized signal from the sensor 32. For example, the filter 50 can be programmed to discriminate against sixty Hertz (60 Hz) or fifty Hertz (50 Hz) noise from nearby electrical components. The filter 50 can also be programmed to average a predetermined number (e.g., ten) of consecutive signals from the sensor 32 and output a signal representative of the average, or the filter 50 can be a low-pass filter. When the noise filter 50 is a software filter, it can function by averaging a plurality (e.g., ten) of sensor signals in accordance with means well-known in the art.

Also, the filter 50 can be programmed to block a signal from the sensor 32 which greatly varies from the immediately previous signal. A great variance from one signal to the next may indicate an erroneous or spurious signal level. In other words, if a first signal from the sensor indicates an electrode 20 temperature of, e.g., eighty degrees centigrade (80° C.), and a second signal that is immediately temporally after the first indicates an electrode 20 temperature which varies by more than a predetermined amount (e.g., 10° C.) from the first signal, the filter 50 blocks the second signal from further processing. The hardware components, if any, of both the A/D converter 48 and the noise filter 50 can be housed in the cauterizer 10 or source 14. When the filter 50 is a software filter, the software filter 50 can be part of the microprocessor 44.

FIG. 3 also shows that a timer 52 is provided which monitors the length of time the source 14 energizes the electrode 20. The timer 52 generates a signal representative of the length of time of electrode 20 energization and sends this signal to the microprocessor 44. When the length of time exceeds a predetermined time period, e.g., a time period between about ten seconds and forty seconds (10 sec- 40 sec), the microprocessor 44 causes the source 14 to stop energizing the electrode 20.

Additionally, components are provided for measuring the output voltage and current of the source 14 of electricity, and for providing signals representative of the output voltage, current, power, and impedance (and, hence, the voltage, current, power, and tissue impedance at the tip of the electrode 20) to the microprocessor 44. More specifically, a component 54, e.g., a current sensing transformer or resistor, is connected in series between the source 14 of electricity and the electrode 20, and a current rectifier filter ("R/F") 56 samples the voltage upstream and downstream of the component 54. Accordingly, the current R/F 56 outputs a signal representative of the output current of the source 14 of electricity.

Also, a voltage sampling R/F 58 is provided for generating a signal representative of the output voltage of the source 14 of electricity. Advantageously, both the current and voltage R/Fs 56, 58 can be full wave diode rectifiers with associated filtering capacitors connected in a configuration well-known in the art.

FIG. 3 shows that the current and voltage R/Fs 56, 58 are respectively connected to A/D converters 60, 62, each of which is substantially similar to the temperature A/D converter 48. In turn, both A/D converters 60, 62 are connected to the microprocessor 44.

Still referring to FIG. 3, the microprocessor 44 generates an output control signal and sends the control signal to an electrical buffer 64. The buffer 64 is any suitable device which essentially isolates the microprocessor 44 from the source 14 of electricity, and which provides correct driving signals to the source 14.

The output signal from the buffer 64 is sent to the source 14 of electricity to control the output power of the source 14 of electricity. To do this, the control signal can be used to vary the output voltage of the source 14 of electricity, or the modulation of the signal from the source 14 of electricity, by means well-known in the art. For example, the signal from the buffer 64 can be used as the bias signal to a power transistor (not shown) that is part of the output circuitry of the source 14 of electricity. Consequently, as the signal from the buffer 64 changes, the bias of the transistor changes to change the output of the source 14 of electricity.

Figure 4:
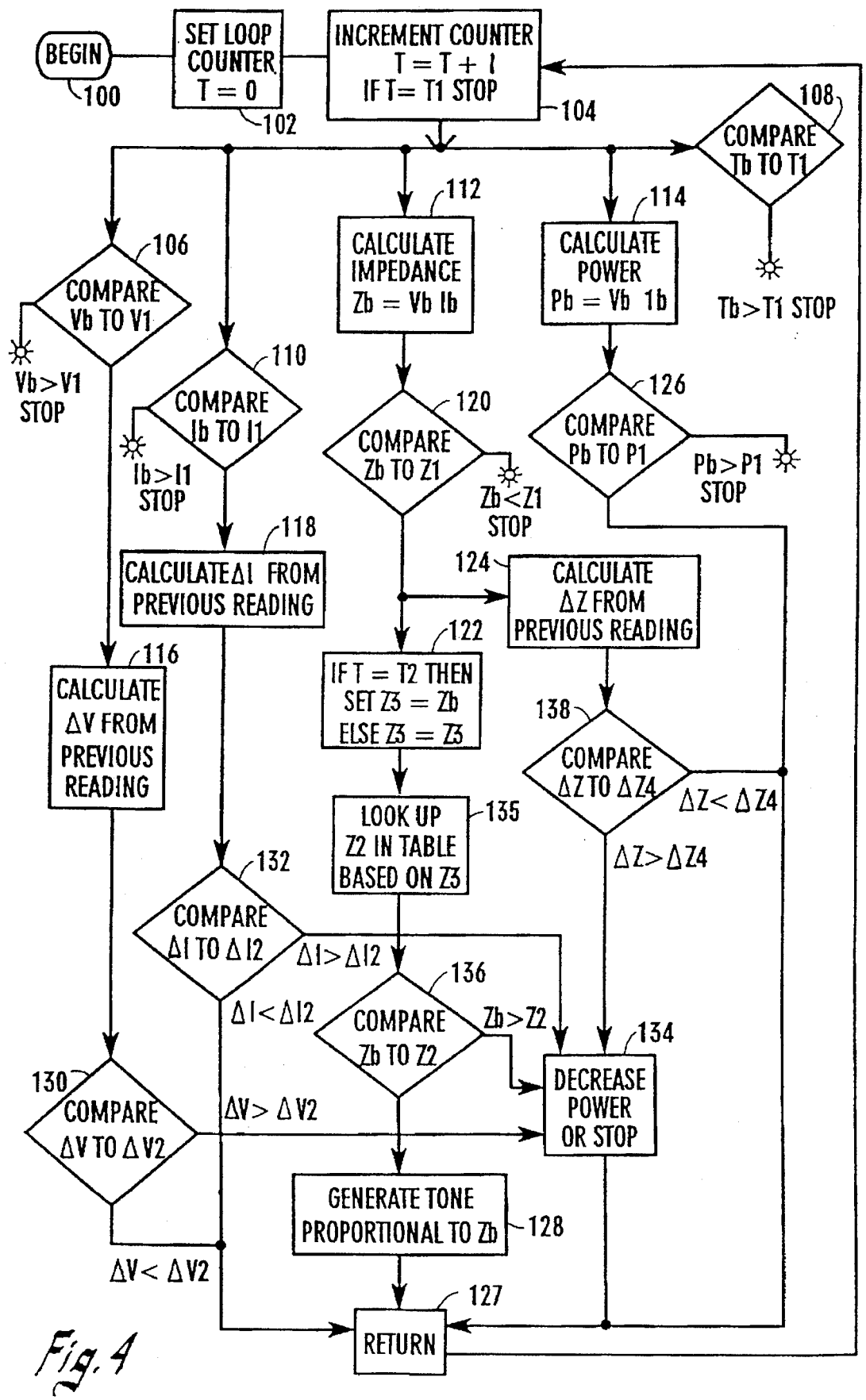
FIG. 4 is a block diagram of the microprocessor logic for generating the control signal.

Now referring to FIG. 4, the details of the operation of the microprocessor 44 can be seen. The microprocessor 44 commences a sampling cycle at begin circle 100. From the circle 100, the microprocessor proceeds to block 102, wherein a software counter "T" is set equal to zero. Then at block 104, "T" is set equal to T+1. If, at block 104, T equals a predetermined software counter "$T_1$," the microprocessor 44 stops i.e., exits the routine shown in FIG. 4.

Otherwise, the microprocessor 44 proceeds in parallel to decision blocks 106, 108, and 110, and to blocks 112 and 114. At decision blocks 106, 108, 110, the microprocessor 44 retrieves from memory and then respectively compares source 14 of electricity output voltage ($V_b$), electrode 20 temperature ($T_b$), and source 14 of electricity output current ($I_b$) to respective predetermined voltage, temperature, and current setpoints V1, T1, I1. If either $V_b$ or Tb exceeds its predetermined setpoint, or if $I_b$ falls below its predetermined setpoint, the microprocessor 44 generates a control signal to cause the source 14 of electricity to stop energizing the electrode 20. Otherwise, the microprocessor 44 proceeds to blocks 116, 118.

At block 112, on the other hand, the microprocessor 44 calculates the impedance ($Z_b$) of the tissue adjacent the electrode 20 by dividing $V_b$ by $I_b$. Then, the microprocessor 44 moves to decision block 120, where the microprocessor 44 compares $Z_b$ to a predetermined setpoint impedance Z1. If $Z_b$ exceeds Z1, poor electrical connection or poor placement of the electrode 20 may be indicated. In such a case, the microprocessor 44 generates a control signal to cause the source 14 of electricity to stop energizing the electrode 20. As intended by the present invention, the source 14 of electricity is deenergized before $Z_b$ reaches zero (0). Else, the microprocessor 44 proceeds to blocks 122 and 124. In the presently preferred embodiment, Z1 is set equal to about fifty ohms.

It is to be understood that while overall impedance is used in the presently preferred embodiment, the phase difference between $V_b$ and $I_b$ can be measured for determining the capacitive impedance component and resistive impedance component, and then either impedance component can be used in lieu of or in addition to $Z_b$. Indeed, the phase difference between $V_b$ and $I_b$ can be used as an input to the microprocessor 44 in lieu of or in addition to the parameters discussed above.

Likewise, at block 114, the microprocessor 44 calculates the output power ($P_b$) of the source 14 of electricity by multiplying $V_b$ and $I_b$. Then, the microprocessor 44 moves to decision block 126, where the microprocessor 44 compares $P_b$ to a predetermined setpoint power P1. If $P_b$ exceeds P1, the microprocessor 44 generates a control signal to cause the source 14 of electricity to stop energizing the electrode 20. Otherwise, the microprocessor 44 proceeds to return block 127, and thence back to block 104.

At blocks 116 and 118, the microprocessor 44 respectively calculates the difference between $V_b$, $I_b$, and $V_{b-1}$, $I_{b-1}$ to yield $\Delta V$, $\Delta I$, where $V_{b-1}$, $I_{b-1}$ are the respective voltage and current values calculated in the immediately preceding cycle. Alternatively, $V_{b-1}$, $I_{b-1}$ can be averages of the n preceding corresponding values where n=any integer, e.g., ten (10), three (3), etc.

From blocks 116, 118, the microprocessor 44 moves to respective decision blocks 130, 132. At block 130, the microprocessor 44 compares $\Delta V$ to a predetermined voltage difference, i.e., $\Delta V_2$. If $\Delta V$ exceeds $\Delta V_2$, the microprocessor 44 moves to block 134, wherein the microprocessor 44 generates a control signal to cause the source 14 of electricity to deactivate or to reduce its power output by a predetermined increment $\Delta P$, e.g., by two watts to four watts (2 w-4 w). Otherwise, the microprocessor 44 moves to block 127 and thence back to block 104 for another cycle.

Likewise, at block 132, the microprocessor 44 compares $\Delta I$ to a predetermined current difference, i.e., $\Delta I_2$. If $\Delta I$ exceeds $\Delta I_2$, the microprocessor 44 moves to block 134, wherein the microprocessor 44 generates a control signal to cause the source 14 of electricity to reduce its power output by $\Delta P$. Otherwise, the microprocessor 44 moves to block 127 and thence to block 104 for another cycle.

Recall that at block 120 the microprocessor 44 compared $Z_b$ to a predetermined constant impedance setpoint Z1. As shown in FIG. 4 starting at block 122, the microprocessor 44 also compares $Z_b$ to a variable impedance setpoint Z2 which is patient-dependent.

More specifically, at block 122 the microprocessor 44 sets an entering argument variable Z3 equal to $Z_b$ if T equals a predetermined stabilization time period T2. Otherwise, the entering argument variable Z3 is set equal to itself. More specifically, when T<T2, Z3 is set equal to a relatively low default value. When T=T2, Z3 is set equal to $Z_b$, and when T>T2, Z3 remains equal to the value of $Z_b$ set at T=T2. Thus, the entering argument Z3 is patient-dependent. In the preferred embodiment, T2 equals between about two (2) seconds to ten (10) seconds, and the default value of Z3 is equal to about two hundred ohms (200Ω).

Then, the microprocessor 44 moves to block 135, wherein the microprocessor 44 retrieves a predetermined impedance limit Z2 by accessing a data table and using Z3 as the entering argument. A representative table is provided herein as Table 1. From block 135, the microprocessor 44 moves to decision block 136, wherein $Z_b$ is compared to Z2. If $Z_b$ exceeds Z2, the microprocessor 44 moves to block 134 to reduce source 14 of electricity output power or deenergize the electrode 20 altogether, and thence to block 128 to generate a tone representative of $Z_b$. Otherwise, the microprocessor 44 moves directly to block 128 to generate a tone representative of $Z_b$. It is to be understood that while block 128 in FIG. 4 indicates that a tone representative of impedance is generated, the tone or other tones could be generated which are representative of the other parameters discussed herein. From block 128, the microprocessor 44 moves to block 127 and then returns to block 104.

The skilled artisan will appreciate that the operation of the microprocessor 44 at block 122 ensures that the entering argument variable Z3 is set equal to a relatively stabilized $Z_b$. More particularly, for a brief initial stabilization period (T2), power interruption is avoided when minor transients in impedance ($Z_b$) might occur and otherwise cause the microprocessor 44 to deenergize the source 14 of electricity.

Stated differently, the microprocessor 44 reduces source 14 output power during the stabilization time T2 only in the instance when $Z_b$ is less than the initial default value of Z2, which is accordingly set equal to a relatively low (e.g., eight hundred ohms (800Ω)) value.

On the other hand, after the stabilization period T2 elapses, $Z_b$ can be expected to reach a steady state value while the tissue surrounding the probe 11 is treated by the electrode 36. During this treatment period, the entering argument Z3 is defined to be equal to the value of $Z_b$ at time T=T2, and the table look-up of Z2 is thus accomplished using a patient-dependent entering argument Z3.

From block 124, the microprocessor 44 proceeds to decision block 138, wherein the microprocessor 44 compares $\Delta Z$ to a predetermined impedance difference, i.e., $\Delta Z4$. If $\Delta Z$ exceeds $\Delta Z4$, the microprocessor 44 moves to block 134, wherein the microprocessor 44 generates a control signal to cause the source 14 of electricity to reduce its power output by $\Delta P$, and thence to block 127. Otherwise, the microprocessor 44 moves directly to block 127, and thence to block 104 for another cycle.

Thus, at blocks 130, 132, 134 the microprocessor 44 determines whether the time rate of change of $V_b$, $I_b$, or $Z_b$ are excessive, and if so, the microprocessor 44 reduces the output power of the source 14 of electricity, or deenergizes the electrode 20 altogether. The present invention also envisions calculating the time rate of change of temperature $T_b$ in a like manner and reducing the output power of the source 14 of electricity in response to an excessively rapid increase in $T_b$ or in the time rate of change of $T_b$.

The present invention contemplates the above-disclosed operation of the microprocessor 44 because, as recognized by the present invention, the tissue impedance at the tip of the electrode 20, and the temperature of the tip of the electrode 20, is affected by the characteristics of the tissue immediately adjacent the electrode 20.

More particularly, when the tissue has not yet been cauterized, the impedance at the electrode 20 tip is relatively low. In contrast, when the tissue has just undergone cauterization, the impedance at the electrode 20 tip is relatively high. Thus, the output voltage, current, and impedance of the source 14 of electricity are all affected by the cauterization of tissue adjacent the electrode 20. Stated differently, the magnitudes of the output voltage and current of the source 14 of electricity, and the magnitude of the impedance of the tissue adjacent the electrode 20, are dependent upon the body characteristics of the patient. Likewise, the temperature ($T_b$) of the electrode 20 tip also depends in part upon the characteristics of the tissue adjacent the tip of the electrode 20.

Hence, by automatically controlling the output of the source 14 of electricity based upon any one of or a combination of $Z_b$, $I_b$, $V_b$, $P_b$, and $T_b$ (and their respective time derivatives), the present invention ensures that tissue adjacent the venous wall is not damaged any further than necessary to effect cauterization. Also, by precisely controlling the output of the source 14 of electricity, the present invention ensures that tissue is precisely cauterized as appropriate for side branch/varicose vein closure. Alternatively, by automatically generating a tone representative of any one of or a combination of $Z_b$, $I_b$, $V_b$, $P_b$, and $T_b$ and their respective time derivatives, the present invention enables the surgeon to precisely control the source 14.

It is to be further understood that the present invention contemplates establishing power-dependent predetermined setpoints, i.e., setpoints that vary with the manually-established power setting of the source 14 of electricity. Thus, V1, I1, Z1, Z2, Z3, P1, T1, and ΔZ4 can all vary with the power setting of the source 14 of electricity. In such an embodiment, a data table correlating power setting with predetermined setpoints is stored in the electronic memory of the microprocessor 44 for look-up by the microprocessor 44 at the appropriate decision blocks discussed above.

While the particular apparatus for venous ligation as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

TABLE 1

| Z3 (Ohms) | Z2 (Ohms) |
| --- | --- |
| 0–49 | 0 |
| 50–74 | 200 |
| 75–99 | 225 |
| 100–124 | 300 |
| 125–149 | 350 |
| 150–174 | 400 |
| 175–199 | 425 |
| 200–224 | 500 |
| 225–249 | 550 |
| 250–274 | 575 |
| 275–299 | 600 |
| 300–324 | 625 |
| 325–349 | 650 |
| 350–374 | 675 |
| 375–449 | 700 |
| 450–474 | 725 |
| 475–499 | 750 |
| 500–524 | 775 |
| 525–549 | 800 |

TABLE 1-continued

| Z3 (Ohms) | Z2 (Ohms) |
| --- | --- |
| 550–574 | 825 |
| 575–599 | 850 |
| 600–638 | 900 |

What is claimed is:

1. A method for treating a varicose vein, comprising the steps of:

(a) providing an electrode;

(b) percutaneously advancing the electrode into the varicose vein such that the electrode is juxtaposed with the wall of the varicose vein;

(c) establishing contact between the wall of the varicose vein and the electrode by manually pressing the vein; and (d) energizing the electrode until the vein collapses around the electrode to thereby block blood flow through the vein.

2. The method of claim 1, wherein the electrode is energized by a power supply, and the method further comprises the step of determining the electrical impedance of the tissue adjacent the electrode.

3. The method of claim 1, further comprising the step of automatically reducing energization of the electrode when the impedance equals a predetermined value.

4. The method of claim 3, wherein the energizing step is accomplished without perforating the vein.

5. The method of claim 1, wherein the varicose vein defines a diameter of between about two millimeters and eight millimeters (2 mm–8 mm), and the method further comprises of establishing the length of the electrode to be approximately equal to the diameter of the varicose vein.

* * * * *